(12) United States Patent
Chen et al.

(10) Patent No.: US 8,375,937 B2
(45) Date of Patent: Feb. 19, 2013

(54) INTESTINAL TRACT PUSHING APPARATUS FOR ULTRASONIC THERAPY

(75) Inventors: Wenzhi Chen, Chongqing (CN); Diyuan Hu, Chongqing (CN); Chunliang Zhao, Chongqing (CN)

(73) Assignee: Chongqing Ronghai Medical Ultrasound Industry Ltd., Chongqing (CN)

( * ) Notice: Subject to any disclaimer, the term of this patent is extended or adjusted under 35 U.S.C. 154(b) by 368 days.

(21) Appl. No.: 12/680,384

(22) PCT Filed: Jun. 20, 2008

(86) PCT No.: PCT/CN2008/001205
§ 371 (c)(1),
(2), (4) Date: May 7, 2010

(87) PCT Pub. No.: WO2009/039721
PCT Pub. Date: Apr. 2, 2009

(65) Prior Publication Data
US 2010/0307486 A1      Dec. 9, 2010

(30) Foreign Application Priority Data
Sep. 27, 2007   (CN) .......................... 2007 1 0152549

(51) Int. Cl.
*A61F 5/24*   (2006.01)
*A61B 8/00*   (2006.01)
(52) U.S. Cl. ...................................... 128/98.1; 600/437

(58) Field of Classification Search ................. 128/98.1, 128/877, 879; 601/2–4, 33–36, 46–47; 600/437–472, 407; 602/5, 16, 19–21; 482/111–112, 114, 118
See application file for complete search history.

(56) References Cited

U.S. PATENT DOCUMENTS

| | | | | |
|---|---|---|---|---|
| 3,598,114 A | * | 8/1971 | Lewis | .............................. 602/19 |
| 7,125,387 B2 | | 10/2006 | Kawabata et al. | |
| 7,645,244 B2 | * | 1/2010 | Mason et al. | ...................... 601/2 |

FOREIGN PATENT DOCUMENTS

| | | |
|---|---|---|
| CN | 2335573 Y | 9/1999 |
| CN | 2343975 Y | 10/1999 |
| CN | 2517387 Y | 10/2002 |
| EP | 1395171 B1 | 4/2006 |
| JP | 2006247214 | 9/2006 |

* cited by examiner

*Primary Examiner* — Kevin C Sirmons
*Assistant Examiner* — Ophelia A Hawthorne
(74) *Attorney, Agent, or Firm* — The Webb Law Firm

(57) ABSTRACT

The present invention discloses an intestinal tract pushing apparatus for ultrasonic therapy. The intestinal tract pushing apparatus includes a pushing member and an acoustically transparent member. One end of said acoustically transparent member is connected to a buckling strip, and the other end of the acoustically transparent member is connected to an adhesive strip. The acoustically transparent member is bound to the human abdomen by virtue of the adhesive fastening of the buckling strip and the adhesive strip. The pushing member employs a hydraulic system.

9 Claims, 4 Drawing Sheets

INTESTINAL TRACT PUSHING APPARATUS FOR ULTRASONIC THERAPY

FIELD OF THE INVENTION

The present invention belongs to the field of ultrasonic therapy, relates to an apparatus for ultrasonic therapy, and particularly relates to an intestinal tract pushing apparatus for ultrasonic therapy which pushes the intestinal tract in vitro during the ultrasonic therapy.

BACKGROUND OF THE INVENTION

In the clinical application of ultrasound to treating hysteromyoma, when the uterus is monitored by an imaging apparatus (e.g. magnetic resonance imaging (MRI)), the solid substance in intestinal tract which is located in front of the uterus may interfere the imaging effect; when hysteromyoma is treated with high intensity focused ultrasound, the ultrasonic waves penetrate through the lower abdomen of the human body and are focused in the target region in uterus. However, the intestinal tract contains air. When the ultrasonic waves pass through the intestinal tract, they are reflected between the air and intestinal wall, resulting in energy deposition that may cause injuries to the intestinal wall which is close to the uterus; meanwhile, the ultrasonic energy to uterus is reduced so that the energy intensity can not satisfy the therapeutic requirement. This problem causes great interference to the security and effectiveness of treating hysteromyoma with ultrasonic waves.

Therefore, the influence caused by the solid substance and gas in the intestinal tract located in front of the uterus should be reduced in the therapy. Usually, consideration can be given to push the intestinal tract in vitro, offset the intestinal tract in front of the uterus and disperse it upwards and to both sides by use of a pushing force, so that the monitoring by the magnetic resonance imaging will not be affected by the solid substance in the intestinal tract; meanwhile, the ultrasonic waves can penetrate through the lower abdomen without any interference by the intestinal tract and the air therein and are focused in the uterus.

A Chinese patent (publication date: Sep. 1, 1999; publication number: CN 2335573Y) disclosed an intestinal tract pushing apparatus for treating hysteromyoma. Said apparatus is a water bag used in B-mode ultrasonic imaging monitoring, the water bag is sealed by a metal seal ring, and the intestinal tract is pushed by the water bag. In order to make the water bag keep contact with the human body, two hooks are employed to clamp and fix the seal ring with two side lugs, the human body and a bottom board, but it is inconvenient to connect or adjust them; moreover, the seal ring enlarges the volume of the apparatus, thereby it is inconvenient to carry the apparatus, and the shape of the water bag is fairly restricted.

SUMMARY OF THE INVENTION

Aiming at the above deficiency in the prior art, the technical problem to be solved by the present invention is to provide an intestinal tract pushing apparatus for ultrasonic therapy which can push the intestinal tract in front of the uterus in vitro conveniently and which can improve the security and effectiveness of treating hysteromyoma with ultrasound.

The technical solution of solving the technical problem in the present invention is that the intestinal tract pushing apparatus includes a pushing member and an acoustically transparent member, one end of said acoustically transparent member is connected to a buckling strip, and the other end of the acoustically transparent member is connected to an adhesive strip, and the acoustically transparent member is bound to the human abdomen through fastening the buckling strip and the adhesive strip.

Said buckling strip may include a buckling strip cloth, a first velcro buckling strip on the buckling strip cloth and a buckling strip connector for connecting the buckling strip to the acoustically transparent member; said adhesive strip includes an adhesive strip cloth, a first velcro adhesive strip on the adhesive strip cloth and an adhesive strip connector for connecting the adhesive strip to the acoustic permeable member; and said first velcro buckling strip is adhesively fastened to the first velcro adhesive strip. Wherein, the buckling strip cloth and the adhesive strip cloth may be made of tensile-resistant material.

Preferably, the buckling strip cloth has a shape of strap which is narrow on one end and is wide on the other end, the first velcro buckling strip is fixed to the narrow end of the buckling strip cloth, the buckling strip connector is provided on the wide end of the buckling strip cloth, the buckling strip connector includes a short adhesive buckling strip which is fixed on one end and is movable on the other end, a latch hook with both ends fixed to the buckling strip cloth, a buckle with a through hole in the middle part and with an opening on one end, the fixed end of the short adhesive buckling strip passes through the hollow part of the latch hook, one side of the fixed end is fixed to the buckling strip cloth, and a second velcro buckling strip is fixed to the other side of the fixed end, a second velcro adhesive strip is fixed to the tip of the movable end of the short adhesive buckling strip, and said movable end passes back through the hollow part of the latch hook after it passes through the through hole in the middle part of the buckle, so that the second velcro adhesive strip is adhesively fastened to the second velcro buckling strip on the fixed end, and one side edge of the acoustically transparent member is clip-connected into the opening of the buckle. Preferably, the adhesive strip cloth has a shape of strap which is narrow on one end and is wide on the other end, a first velcro adhesive strip is fixed to the narrow end of the adhesive strip cloth, the adhesive strip connector is provided on the wide end of the adhesive strip cloth, the adhesive strip connector includes a short adhesive buckling strip which is fixed on one end and is movable on the other end, a latch hook with both ends fixed to the adhesive strip cloth, a buckle with a through hole in the middle part and with an opening on one end, the fixed end of the short adhesive buckling strip passes through the hollow part of the latch hook, a bottom surface of the fixed end is fixed to the adhesive strip cloth, and a second velcro buckling strip is fixed to the other surface of the fixed end, a second velcro adhesive strip is fixed to the tip of the movable end of the short adhesive buckling strip, and said movable end passes back through the hollow part of the latch hook after it passes through the through hole in the middle part of the buckle, so that the second velcro adhesive strip is adhesively fastened to the second velcro buckling strip on the fixed end, and the other side edge of the acoustically transparent member is clip-connected into the opening of the buckle.

The acoustically transparent member may employ an acoustically transparent film, long and short side edges of said acoustically transparent film wrap long flanging press bars and short flanging press bars respectively, said two short flanging press bars are provided in the openings of the buckles on the buckling strip and the adhesive strip respectively, and said long flanging press bars are wrapped in the acoustically transparent film along the long side edges of the acoustically transparent film and are fixed inside the long side edges after being turned several rounds. Further preferably, said buckling strip connector is provided symmetrically with the adhesive strip connector, and a plurality of the buckling strip connectors and a plurality of the adhesive strip connectors which are provided symmetrically with each other may be employed respectively.

Said pushing member employs a hydraulic system which may include a water bag, and a bush and a gland which are capable of sealing an open end of the water bag, the bush and the gland are connected integrally, and a joint which can be connected to the external water pipe is provided on said gland. Preferably, said water bag is made of emulsion material.

In the present invention, the buckling strip and the adhesive strip are connected to each other into a ribbon shaped adhesive buckling strip through the acoustically transparent member, and the pushing member itself is formed into an integral body. The waist of a patient is surrounded by the adhesive buckling strip formed by the buckling strip, the acoustically transparent member and the adhesive strip, and the hydraulic system is inserted between the adhesive buckling strip and the abdomen of the human body. The length of said adhesive buckling strip can be adjusted, therefore, the waist and abdomen of the human body are tightened and fixed by the adhesive buckling strip, the intestinal tract is pushed in vitro and extruded along both sides and upside and backside of the uterus, and the relevant tissues in vivo cling closely to each other, so that the influence on sound energy and imaging caused by the substances in vivo, particularly the gas, solid or the like in the intestinal tract is effectively eliminated, the attenuation of sound energy is reduced, the effective treatment depth is increased, and the treatment effect is secured.

The velcro adhesive buckling strip makes it easy for the doctor to perform the releasing and fastening operations, and with its help, the adhesive buckling strip with a fixed length can form different circumferential lengths to be adapted for patients with different waistlines.

The acoustically transparent member employs an acoustically transparent film to ensure the normal breathing of the skin under the adhesive buckling strip, to ensure an enough tensile force, and to provide a proper acoustically transparent region as well as a more comfortable feeling for the patients. Meanwhile, the tensile force can be controlled conveniently by adjusting the amount of the injected water of the hydraulic system according to requirements for the therapy.

When the next treatment is performed, the vulnerable acoustically transparent member can be replaced rapidly by using a new acoustically transparent film and processing it simply in accordance with the required manner, meanwhile, the buckling strip and the adhesive strip are maintained for further use, thereby the cost of the therapy is reduced partially.

Wherein: 1—buckling strip 11—buckling strip cloth 12—first velcro buckling strip 13—short adhesive buckling strip 14—latch hook 15—second velcro adhesive strip 16—second velcro buckling strip 2—acoustically transparent member 21—acoustically transparent film 22—buckle 23—pressing bar 24—short flanging press bar 25—long flanging press bar 3—adhesive strip 31—adhesive strip cloth 32—first velcro adhesive strip 4—hydraulic system 41—water bag 42—bush 43—O seal ring 44—gland 45—sealing gasket 46—joint

DETAILED DESCRIPTION OF THE PREFERRED EMBODIMENTS

Embodiments of the present invention will be further explained below in detail with reference to the accompanying drawings.

The following embodiments are nonrestrictive embodiments of the present invention:

Embodiment 1

Figure 1:
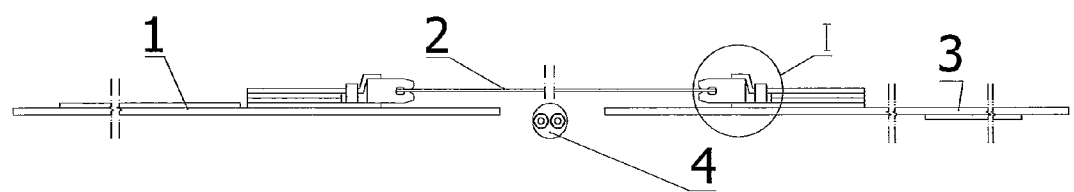
FIG. 1 is a structural front view of an intestinal tract pushing apparatus for ultrasonic therapy of the present invention.
Figure 2:
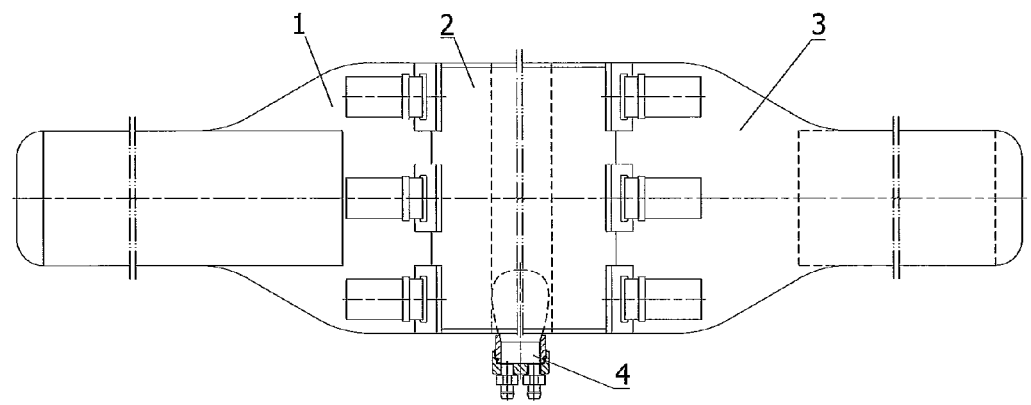
FIG. 2 is a top view of FIG. 1.

FIGS. 1 and 2 are a front view and a top view of an intestinal tract pushing apparatus for ultrasonic therapy of the present invention respectively. The intestinal tract pushing apparatus includes a pushing member and an acoustically transparent member 2. One end of said acoustically transparent member is connected to a buckling strip 1, and the other end is connected to an adhesive strip 3. That is, the buckling strip 1 is connected to the adhesive strip 3 through the acoustically transparent member 2, and the acoustically transparent member 2 is bound to the human abdomen by virtue of the adhesive fastening of the buckling strip 1 and the adhesive strip 3. The pushing member employs a hydraulic system 4 which is independent from the adhesive buckling strip, and the pushing member and the adhesive buckling strip are used cooperatively in therapy.

Figure 3:
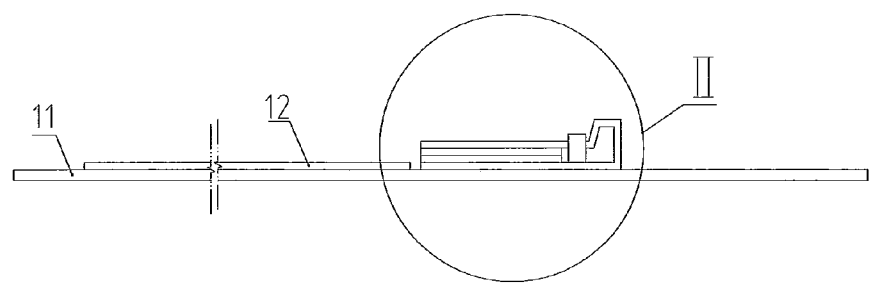
FIG. 3 is a structural front view of a buckling strip 1.
Figure 4:
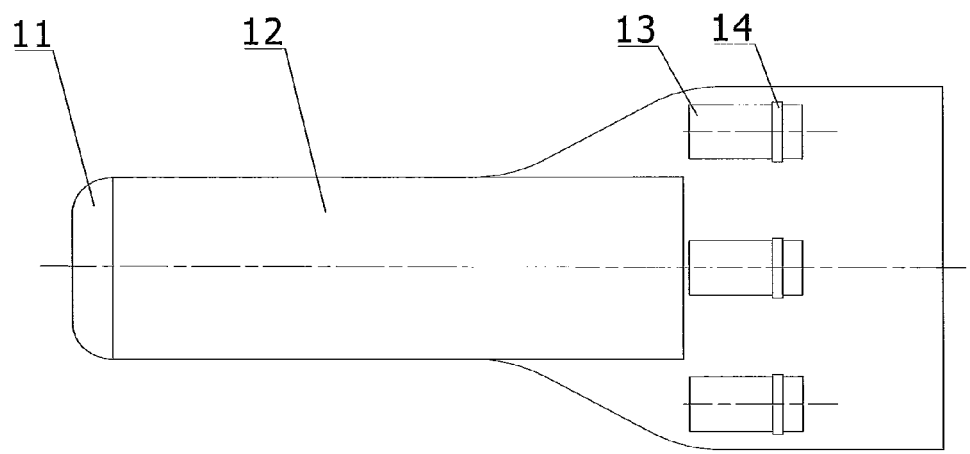
FIG. 4 is a top view of FIG. 3.
Figure 5:
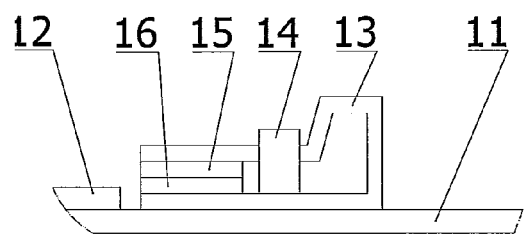
FIG. 5 is an enlarged view of a portion II in FIG. 3.
Figure 9:
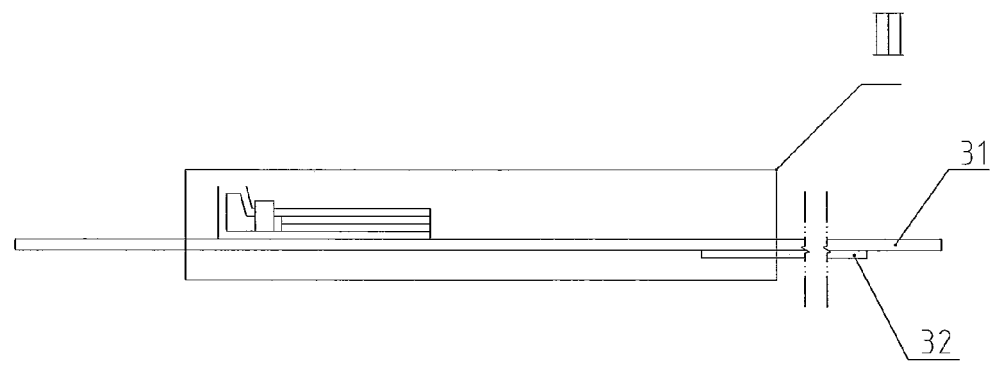
FIG. 9 is a structural front view of an adhesive strip 3.
Figure 10:
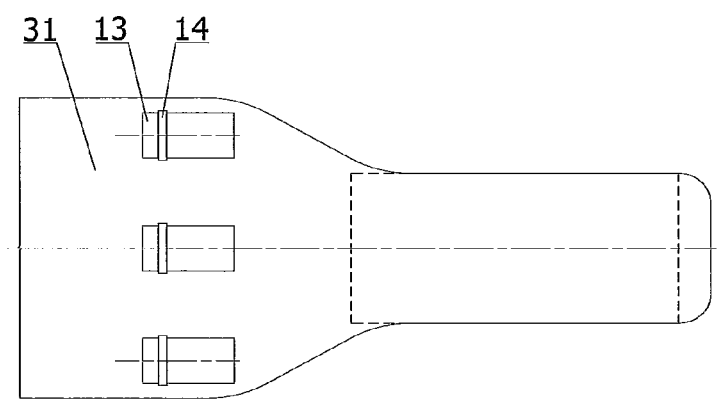
FIG. 10 is a top view of FIG. 9.
Figure 11:
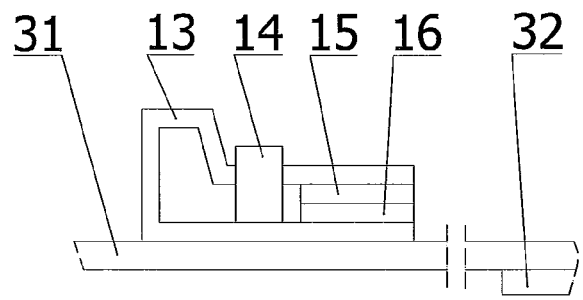
FIG. 11 is an enlarged view of a portion III in FIG. 9.

FIGS. 3 and 4 are a structural front view and a top view of the buckling strip 1 respectively, and FIG. 5 is a schematic diagram of a partial structure of the buckling strip 1. As shown in FIGS. 3, 4 and 5, the buckling strip 1 includes a buckling strip cloth 11, a first velcro buckling strip 12 on the buckling strip cloth 11, and a buckling strip connector for connecting the buckling strip 1 to the acoustically transparent member 2. FIGS. 9 and 10 are a structural front view and a top view of the adhesive strip 3 respectively, and FIG. 11 is a schematic diagram of a partial structure of the adhesive strip 3. The specific structure of the adhesive strip 3 is similar to that of the buckling strip 1. The adhesive strip 3 includes an adhesive strip cloth 31, a first velcro adhesive strip 32 on the adhesive strip cloth 31, and an adhesive strip connector for connecting the adhesive strip 3 to the acoustically transparent member 2. The first velcro buckling strip 12 can be adhesively fastened to the first velcro adhesive strip 32. Wherein, both the buckling strip cloth 11 and the adhesive strip cloth 31 can be made of tensile-resistant material.

As shown in FIG. 4, the buckling strip cloth 11 is at the bottom of the buckling strip 1, and all of other parts on the buckling strip 1 are sewn on the buckling strip cloth 11. The buckling strip cloth 11 has a shape of strap which is narrow on one end and wide on the other end. The first velcro buckling strip 12 is fixed to the narrow end of the buckling strip cloth 11 by being sewn directly, and a buckling strip connector is provided in the same side as that of the first velcro buckling strip 12 on the wide end of the buckling strip cloth 11.

As shown in FIG. 5, the buckling strip connector includes a short adhesive buckling strip 13 which is fixed on one end and is movable on the other end, a latch hook 14, and a buckle 22 with a through hole in the middle part and with an opening on one end. The latch hook 14 employs a cloth hook which is formed by fixing both ends of a piece of cloth to the buckling strip cloth 11. The fixed end of the short adhesive buckling strip 13 passes through the hollow part of the latch hook 14, and the end of the short adhesive buckling strip 13 close to the first velcro buckling strip 12 is sewed on the buckling strip cloth 11 to form the fixed end. One side of the fixed end is sewed on the buckling strip cloth 11, and a second velcro buckling strip 16 is fixed to the other side of the fixed end. A second velcro adhesive strip 15 is fixed to the tip of the movable end of the short adhesive buckling strip 13, and said movable end passes back through the hollow part of the latch hook 14 after it passes through the through hole in the middle part of the buckle 22, so that the second velcro adhesive strip 15 is adhesively fastened to the second velcro buckling strip 16 on the fixed end. As shown in FIG. 4, a plurality of the latch hooks 14 and the short adhesive buckling strips 13 with the same number are employed in the present embodiment to strengthen the fixing effect.

As shown in FIGS. 9, 10 and 11, an adhesive strip cloth 31 is at the bottom of the adhesive strip 3, and all of other parts on the adhesive strip 3 are sewed on the adhesive strip cloth 31. The adhesive strip cloth 31 has a shape of strap which is narrow on one end and wide on the other end. A first velcro adhesive strip 32 is fixed to the narrow end of the adhesive strip cloth 31 by being sewn directly, and an adhesive strip connector is provided in the opposite side to that of the first velcro adhesive strip 32 on the wide end of the adhesive strip cloth 31. Wherein, the first velcro adhesive strip 32 is sewed on the opposite surface to the surface on which the adhesive strip connector and the adhesive cloth 31 are sewn up, meanwhile, the opposite sewing surface is opposite to the surface on which the first velcro buckling strip 12 and the buckling strip cloth 11 are sewn up.

Wherein, the structure of the adhesive strip connector is similar to that of the buckling strip connector. As shown in FIG. 11, the adhesive strip connector includes a short adhesive buckling strip 13 which is fixed on one end and is movable on the other end, a latch hook 14, and a buckle 22 with a through hole in the middle part and with an opening on one end. The latch hook 14 employs a cloth hook which is formed by fixing both ends of a piece of cloth to the adhesive strip cloth 31. The fixed end of the short adhesive buckling strip 13 passes through the hollow part of the latch hook 14, and the end of the short adhesive buckling strip 13 close to the first velcro adhesive strip 32 is sewed to the adhesive strip cloth 31 to form the fixed end. One side of the fixed end is sewed on the adhesive strip cloth 31, and a second velcro buckling strip 16 is fixed on the other side of the fixed end. A second velcro adhesive strip 15 is fixed to the tip of the movable end of the short adhesive buckling strip 13, said movable end passes back through the hollow part of the latch hook 14 after it passes through the through hole in the middle part of the buckle 22, so that the second velcro adhesive strip 15 is adhesively fastened to the second velcro buckling strip 16 on the fixed end.

As shown in FIG. 11, a plurality of the latch hooks 14 and the short adhesive buckling strips 13 with the same number are employed in the present embodiment to strengthen the fixing effect.

Wherein, a plurality of the buckling strip connectors on the buckling strip cloth 11 are provided symmetrically with a plurality of the adhesive strip connectors on the adhesive strip cloth 31.

Figure 6:
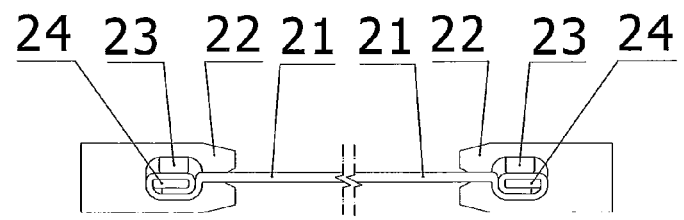
FIG. 6 is a structural front view of an acoustically transparent member 2.
Figure 7:
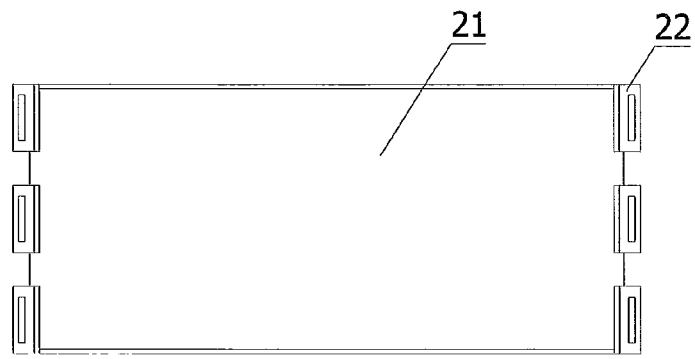
FIG. 7 is a top view of FIG. 6.

FIGS. 6 and 7 are a structural front view and a top view of the acoustically transparent member 2 respectively. In the present embodiment, the acoustically transparent member 2 employs an acoustically transparent film 21.

Figure 8:
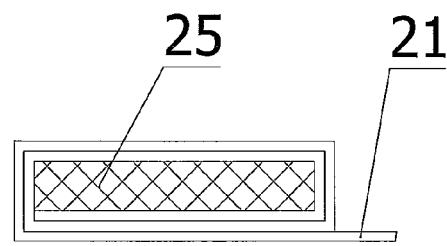
FIG. 8 is a schematic diagram showing a position relation between an acoustically transparent film 21 and a long flanging press bar 25.

Two long flanging press bars 25 (the long flanging press bar 25 is a narrow strip with a length equal to or slightly less than that of long side edge of the acoustically transparent film 21) made of flexible material are pasted on the two long side edges of the acoustically transparent film 21 respectively. As shown in FIG. 8, the long flanging press bars 25 are wrapped in the acoustically transparent film 21 tightly along the long side edges thereof, and the acoustically transparent film 21 is pasted and fixed after the long flanging press bars 25 are turned several rounds. The long flanging press bars 25 are employed to strengthen the long side edges for preventing the acoustically transparent film 21 from being broken by the tensile force in use.

Two short flanging press bars 24 made of flexible material are pasted on two short side edges of the acoustically transparent film 21 respectively. The short flanging press bars 24 are wrapped in the acoustically transparent film 21 along the short side edges thereof, and the acoustically transparent film 21 is pasted and fixed after the short flanging press bars 24 are turned several rounds. Wherein, after the short flanging press bars 24 are wrapped by the two short side edges of the acoustically transparent film 21, said two short flanging press bars 24 are inserted into the openings of the buckles 22 on the buckling strip 1 and the adhesive strip 3 on both ends of the acoustically transparent film 21 respectively, then pressing bars 23 are inserted into the voids in the openings to fill said voids. The short flanging press bars 24 are employed to thicken the short side edges so as to be inserted into the buckles 22, so that the buckles 22 are connected to the acoustically transparent film 21 better.

A plurality of the buckles 22 are provided for strengthening the fixing effect and the number of them are the same as that of the latch hooks 14 and the short adhesive buckling strips 13 on the both ends of the acoustically transparent film 21. Since the acoustically transparent film 21 is consumable item which is single-used, the buckles 22 can be reused, while other members shall be replaced.

Figure 12:
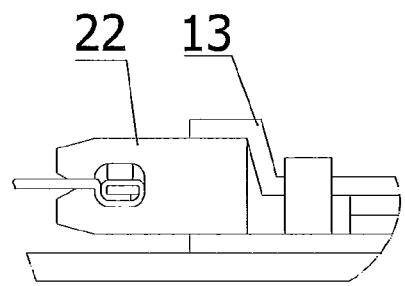
FIG. 12 is an enlarged view of a portion I in FIG. 1.

As shown in FIG. 12, when the acoustically transparent film 21 is connected to the adhesive strip 3, the short adhesive buckling strip 13 in the adhesive strip 3 is released, and the movable end of the short adhesive buckling strip 13 passes through the opened hole in the middle part of the buckle 22. Then, as shown in FIG. 11, after the short adhesive buckling strip 13 passes through the hollow part of the latch hook 14 in the adhesive strip 3, the second velcro adhesive strip 15 is adhered to the second velcro buckling strip 16. After each buckle 22 is fixed to the short adhesive buckling strip 13, the connection of the acoustically transparent film 21 to the adhesive strip 3 is realized. The buckling strip 1 is connected to the acoustically transparent film 21 by the similar method, then, an adhesive buckling strip shown in FIG. 1 is formed by the buckling strip 1, the acoustically transparent film 21 and the adhesive strip 3.

Figure 13:
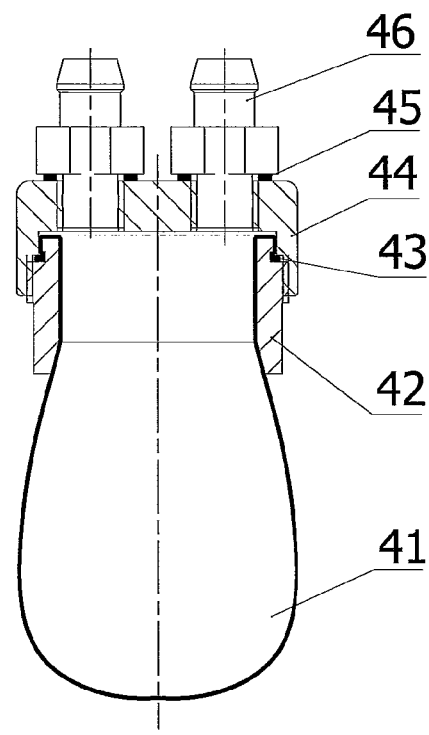
FIG. 13 is a structural schematic diagram of a hydraulic system 4.

FIG. 13 is a structural schematic diagram of the hydraulic system 4. The hydraulic system 4 includes a water bag 41, and a bush 42 and a gland 44 which are capable of sealing the open end of the water bag. The bush 42 and the gland 44 are connected integrally, and a joint 46 is provided on said gland 44. In this embodiment, the water bag 41 is made of emulsion material. The opening of water bag 41 is counter-fastened to the bush 42 and is encased by an O seal ring 43. The bush 42 is connected and secured to the gland 44 with screws. A sealing gasket 45 is provided between the gland 44 and the joint 46 for preventing leakage. The joint 46 on the gland 44 can be connected to a water pipe of external pressure water.

During therapy, a patient lies down on a treatment bed. The adhesive buckling strip shown in FIG. 1 surrounds the waist of the patient to ensure the acoustically transparent film 21 opposite rightly to the upper side of the abdomen of the pelvic cavity, and the water bag 41 is counter-inserted between the abdomen of the patient and the acoustically transparent film 21. The position of the water bag 41 is adjusted so that the water bag 41 is laid flat vertically in the middle lower part of the pelvic cavity. The adhesive buckling strip is tightened to adhere the first velcro buckling strip 12 on the buckling strip 1 to the first velcro adhesive strip 32 on the adhesive strip 3. Water is injected into the hydraulic system 4 to make the water bag 41 swell. Under the tension of the water bag 41 and the pressure of the adhesive buckling strip, the intestinal tract is pushed in vitro along both sides of the uterus and towards the upside and backside of the uterus. Then, the imaging detection operation before the ultrasonic therapy can be performed (e.g. magnetic resonance imaging (MRI) apparatus is employed).

Since the intestinal tract has been pushed away from the front of the detected organ, the factors interfering with the imaging outcomes in a monitoring process are greatly reduced, so that the determination of the position to be treated before ultrasonic therapy is more accurate. In the subsequent ultrasonic therapy, an ultrasound applicator radiates from the external to the target region of therapy, the ultrasonic waves for therapy enter the human body after passing through the acoustically transparent film 21 and the water bag 41, and the gas in the intestinal tract will not block the transmission pathway of ultrasonic waves, so that the intensity and safety of the therapy are ensured.

The invention claimed is:

1. An intestinal tract pushing apparatus for ultrasonic therapy, comprising a pushing member and an acoustically transparent member, wherein one end of said acoustically transparent member is connected to a buckling strip, and the other end of the acoustically transparent member is connected to an adhesive strip, and the acoustically transparent member is configured to be bound to the human abdomen by virtue of adhesive fastening of the buckling strip and the adhesive strip,
wherein said buckling strip includes a buckling strip cloth, a first hook and loop fastener buckling strip on the buckling strip cloth and a buckling strip connector for connecting the buckling strip to the acoustically transparent member; said adhesive strip includes an adhesive strip cloth, a first hook and loop fastener adhesive strip on the adhesive strip cloth and an adhesive strip connector for connecting the adhesive strip to an acoustic permeable member; and said first hook and loop fastener buckling strip is adhesively fastened to the first hook and loop fastener adhesive strip.

2. The intestinal tract pushing apparatus for ultrasonic therapy according to claim 1, wherein the buckling strip cloth has a strap shape which is narrow on one end and is wide on the other end, the first hook and loop fastener buckling strip is fixed to the narrow end of the budding strip cloth, and the buckling strip connector is provided on the wide end of the buckling strip cloth; the budding strip connector includes a short adhesive buckling strip which is fixed on one end and is movable on the other end, a latch hook with both ends fixed to the buckling strip cloth, and a buckle with a through hole in the middle part and with an opening on one end; the fixed end of the short adhesive buckling strip passes through a hollow part of the latch hook, one side of the fixed end is fixed to the buckling strip cloth, and a second hook and loop fastener buckling strip is fixed to the other side of the fixed end, a second hook and loop fastener adhesive strip is fixed to the tip of the movable end of the short adhesive buckling strip, and said movable end passes back through the hollow part of the latch hook after it passes through the through hole in the middle part of the buckle, so that the second hook and loop fastener adhesive strip is adhesively fastened to the second hook and loop fastener buckling strip on the fixed end, and one side edge of the acoustically transparent member is clip-connected into the opening of the buckle.

3. The intestinal tract pushing apparatus for ultrasonic therapy according to claim 2, wherein the adhesive strip cloth has a strap shape which is narrow on one end and is wide on the other end, a first hook and loop fastener adhesive strip is fixed to the narrow end of the adhesive strip cloth, and the adhesive strip connector is provided on the wide end of the adhesive strip cloth; the adhesive strip connector includes a short adhesive buckling strip which is fixed on one end and is movable on the other end, a latch hook with both ends fixed to the adhesive strip cloth, and a buckle with a through hole in the middle part and with an opening on one end; the fixed end of the short adhesive buckling strip passes through the hollow part of the latch hook, a bottom surface of the fixed end is fixed to the adhesive strip cloth, and a second hook and loop fastener buckling strip is fixed to the other surface of the fixed end, a second hook and loop fastener adhesive strip is fixed to the tip of the movable end of the short adhesive buckling strip, and said movable end passes back through the hollow part of the latch hook after it passes through the through hole in the middle part of the buckle, so that the second hook and loop fastener adhesive strip is adhesively fastened to the second hook and loop fastener buckling strip on the fixed end, and the other side edge of the acoustically transparent member is clip-connected into the opening of the buckle.

4. The intestinal tract pushing apparatus for ultrasonic therapy according to claim 3, wherein said buckling strip connector is provided symmetrically with the adhesive strip connector.

5. The intestinal tract pushing apparatus for ultrasonic therapy according to claim 4, wherein a plurality of the buckling strip connectors and a plurality of the adhesive strip connectors which are provided symmetrically with each other are employed respectively.

6. The intestinal tract pushing apparatus for ultrasonic therapy according to claim 3, wherein the acoustically transparent member employs an acoustically transparent film, long and short side edges of said acoustically transparent film wrap long flanging press bars and short flanging press bars respectively, said two short flanging press bars are provided in the openings of the buckles on the buckling strip and the adhesive strip respectively, and said long flanging press bars are wrapped in the acoustically transparent film along the long side edges of the acoustically transparent film and are fixed inside the long side edges after being turned several rounds.

7. The intestinal tract pushing apparatus for ultrasonic therapy according to claim 1, wherein said pushing member employs a hydraulic system which includes a water bag, and a bush and a gland which are capable of sealing an open end of the water bag, the bush and the gland are connected integrally, and a joint which can be connected to the external water pipe is provided on said gland.

8. The intestinal tract pushing apparatus for ultrasonic therapy according to claim 7, wherein said water bag is made of emulsion material.

9. The intestinal tract pushing apparatus for ultrasonic therapy according to claim 1, wherein the buckling strip cloth and the adhesive strip cloth are made of material having tensile resistance.

* * * * *

UNITED STATES PATENT AND TRADEMARK OFFICE
CERTIFICATE OF CORRECTION

PATENT NO. : 8,375,937 B2  
APPLICATION NO. : 12/680384  
DATED : February 19, 2013  
INVENTOR(S) : Wenzhi Chen et al.

Page 1 of 1

It is certified that error appears in the above-identified patent and that said Letters Patent is hereby corrected as shown below:

In the Claims:

Column 7, Line 52, Claim 2, delete "budding" and insert -- buckling --

Column 7, Line 54, Claim 2, delete "budding" and insert -- buckling --

Signed and Sealed this
Fourteenth Day of May, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,375,937 B2  Page 1 of 1
APPLICATION NO. : 12/680384
DATED : February 19, 2013
INVENTOR(S) : Chen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 407 days.

Signed and Sealed this

First Day of September, 2015

Michelle K. Lee
*Director of the United States Patent and Trademark Office*